United States Patent
Du et al.

(10) Patent No.: US 8,633,023 B2
(45) Date of Patent: Jan. 21, 2014

(54) METHOD OF LIQUID NITROGEN SURFACE VITRIFICATION

(75) Inventors: Fuliang Du, Mansfield, CT (US); Jie Xu, Centerville, VA (US); Juan Moreno, College Station, TX (US)

(73) Assignee: Inguran, LLC, Navasota, TX (US)

( * ) Notice: Subject to any disclaimer, the term of this patent is extended or adjusted under 35 U.S.C. 154(b) by 0 days.

(21) Appl. No.: 13/818,072

(22) PCT Filed: Aug. 17, 2011

(86) PCT No.: PCT/US2011/048095
§ 371 (c)(1),
(2), (4) Date: Feb. 20, 2013

(87) PCT Pub. No.: WO2012/024408
PCT Pub. Date: Feb. 23, 2012

(65) Prior Publication Data
US 2013/0157362 A1 Jun. 20, 2013

Related U.S. Application Data (60) Provisional application No. 61/375,716, filed on Aug. 20, 2010.

(51) Int. Cl.
| | |
|---|---|
| C12N 5/07 | (2010.01) |
| C12N 5/073 | (2010.01) |
| C12N 5/075 | (2010.01) |
| A01N 1/02 | (2006.01) |
| C12N 5/02 | (2006.01) |

(52) U.S. Cl.
CPC ............ *A01N 1/0284* (2013.01); *A01N 1/0278* (2013.01); *A01N 1/02* (2013.01); *C12N 5/0604* (2013.01); *C12N 5/0609* (2013.01)
USPC .......................................... 435/374; 435/325

(58) Field of Classification Search
None
See application file for complete search history.

(56) References Cited

U.S. PATENT DOCUMENTS

| | | | |
|---|---|---|---|
| 6,982,172 B2 | 1/2006 | Yang | |
| 2010/0099171 A1* | 4/2010 | Huang et al. | 435/283.1 |

FOREIGN PATENT DOCUMENTS

| | | |
|---|---|---|
| EP | 1131998 A1 | 9/2001 |
| EP | 2156735 A1 | 2/2010 |

(Continued)

OTHER PUBLICATIONS

Nedambale et al., "Bovine blastocyst development in vitro: timing, sex, and viability following vitrificiation." Biol Reprod, 2004, 71, 1671-1676.

(Continued)

*Primary Examiner* — Ruth Davis
*Assistant Examiner* — Emily Cordas
(74) *Attorney, Agent, or Firm* — Cindee R. Ewell; Ryan Christensen (57) ABSTRACT

A method of liquid nitrogen surface vitrification requiring an embryo washed in a rinsing medium, then incubated in a base medium and incubated in a hold medium before being washed in a vitrification medium and produced into a vitrification droplet (270). For forming the droplet, vitrification medium (210), an intermediary fluid such as air, followed by vitrification medium containing at least one embryo (250) are aspirated into the channel. The vitrification droplet consequently can contain an air bubble (220). The vitrification droplet can be produced from an instrument with a channel and dropped directly into liquid phase nitrogen producing a vitrified droplet. The vitrified droplet can be stored in cryo-vessels, and warmed for revitalization of biological function of vitrified biological cell mass or tissues, such as oocytes and/or embryos.

9 Claims, 4 Drawing Sheets

(56) References Cited

FOREIGN PATENT DOCUMENTS

| WO | 0149112 | 7/2001 |
|---|---|---|
| WO | 2007123720 A2 | 11/2007 |
| WO | 2008040022 | 4/2008 |

OTHER PUBLICATIONS

Mucci et al., "Effect of estous cow serum during boine embryo culture on blastocyst development and cryotolerance after slow freezing or vitirification." Theriogenology, 2006, 65, 1551-1562.
Kwun et al., "Effects of exogenous hexoses on bovine in vitro fertilized and cloned embryo developmen: Improved blastocyst formation after glucose replacement with fructose in a serum-free culture medium." Mol Reprod Dev., 2003, 65, 167-174.
Ushijima et al., "Cryopreservation of bovine pre-morula-stage in vitro matured/in vitro fertilized embryos after delipidation and before use in nucleus transfer." Biol Reprod, 1999, 60, 534-539.
Murakami et al., "Effects of centrifugation and lipid removal on the cryopreservation of in vitro produced bovine embryos at the eight-cell stage." Cryobiology, 1998, 36, 206-212.
Barcelo et al., "Effects of either glucose or fructose and metabolic regulators on bovine embryo development and lipid accumulation in vitro." Mol Reprod Dev, 2007, 74, 1406-1418.
Seidel et al., "Modifying oocytes and embryos to improve their cryopreservation." Theriogenology, 2006, 65, 228-235.
Block et al., "The effect of in vitro treatment of bovine embryos with IGF-1 on subsequent development in utero to Day 14 of gestation." Theriogenology 2007, 68, 153-161.
Chaubal et al., "Effect of addition of fructose to the culture medium on development of bovine in vitro produced sexed embryos." Reprod Fertil Dev, 2009, 21 (Abstract).
Dobrinsky et al.," Advancements in cryopreservation of domestic animal embryos." Theriogenology, 2002, 57, 285-302.
Sommerfeld et al., "Cryopreservation of bovine in vitro produced embryos using ethylene glycol in controlled freezing or vitrification." Cryobiology, 1999, 38, 95-105.
Massip, A., "Cryopreservation of embryos of farm animals." Reprod Domest Anim, 2001, 36, 49-55.
Lane et al., "Vitrification of mouse and human blastocysts using a novel cryoloop container-less technique." Fertil Steril, 1999, 72, 1073-1078.
Cervera et al., "Vitrification of zona-free rabbit expanded or hatching blastocysts: a possible model for human blastocysts." Hum Reprod, 2003, 18, 2151-2156.
Drost., "Conception rates after artificial insemination or embryo transfer in lactating dairy cows during summer in Florida." Theriogenology, 1999; 52, 1161-1167.
Al-Katanani et al., "Pregnancy rates following timed embryo transfer with fresh or vitrified in vitro produced embryos in lactating dairy cows under heat stress conditions." Theriogenology, 2002, 58, 171-182.
Dochi et al., "The use of embryo transfer to produce pregnancies in repeat-breeding dairy cattle." Theriogenology 2008, 69, 124-128.
Du et al., "The cell agglutination agent, phytohemagglutinin-L, improves the efficiency of somatic nuclear transfer cloning in cattle (*Bos taurus*)." Theriogenology, 2006, 65, 642-657.
Vajta et al., "Open Pulled Straw (OPS) vitrification: a new way to reduce cryoinjuries of bovine ova and embryos." Mol Reprod Dev, 1998, 51, 53-58.
Vajta et al., "The effect of media, serum and temperature on in vitro survival of bovine blastocysts after Open Pulled Straw (OPS) vitrification." Theriogenology, 1999, 52, 939-948.
Dinnyes et al., "High developmental rates o vitrified bovine oocytes following parthenogenetic activation,. in vitro fertilization, and somatic cell nuclear transfer." Biol Reprod, 2000, 63, 513-518.
Xu et al., "Developmental potential of vitrified Holstein cattle embryos fertilized in vitro with sex-sorted sperm." J Dairy Sci, 2006, 89, 2510-2518.
Nedambale et al., "Comparison on in vitro fertilized bovine embryos cultured in KSOM or SOF and cryopreserved by slow freezing or vitrification" Theriogenology, 2004, 62, 437-449.
Campos-Chillon et al., "Vitrification of early-stage bovine and equine embryos." Theriogenology, 2009, 71, 349-354.
PCT International Search Report and Written Opinion dated Jul. 19, 2012 issued in corresponding PCT Application No. PCT/US2011/048095 (31 pages).
Papis, K. et al, "Factors affecting the survivability of bovine oocytes vitrified in droplets", Theriogenology, vol. 54, No. 5, Sep. 1, 2000, pp. 651-658. (8 pages).
Yang et al, "Development of vitrified-thawed bovine oocytes after in vitro fertilization and somatic cell nuclear transfer" Animal Reproduction Science, Elsevier Science Publishers, Amsterdam, NL, vol. 103, No. 1-2, Nov. 16, 2007, pp. 25-37 (13 pages).
Xu J et al, "Optimizing IVF with sexed sperm in cattle", Theriogenology, Los Altos, CA, US, vol. 71, No. 1, Jan. 1, 2009, pp. 39-47 (9 pages).
Utkan Demirci et al, "Cell encapsulation droplet vitrification", Lab on a Chip, vol. 7, No. 11, Nov. 1, 2007, pp. 1428-1433 (6 pages).
B.S.Yang et al, "Viability of in vitro-derived bovine zygotes cryopreserved in microdrops", Theriogenology, vol. 51, No. 1, Jan. 1, 1999, p. 178 (1 page).
Papis K et al, "The Effect of Gentle Pre-Equilibration on Survival and Development Rates on Survival and Development Rates of Bovine In Vitro Matured Oocytes Vitrified in Droplets", Theriogenology, Jan. 1, 1999, p. 173 (1.
Teraporn Vutyavanich et al, "Closed-system solid surface vitrification versus slow programmable freezing of mouse 2-cell embryos", Journal of Assisted Reproduction and Genetics, vol. 26, No. 5, Jul. 15, 2009, pp. 285-290 (6 pages).
Shinichi Hochi et al, "Effects of Cooling and Warming Rates during Vitrification on Fertilization of in Vitro-Matured Bovine Oocytes", Cryobiology, vol. 41, No. 1, Feb. 1, 2001, pp. 69-73 (5 pages).
Masashige Kuwayama et al, "Highly efficient vitrification method for cryopreservation of human oocytes", Reproductive Biomedicine Online, vol. 11, No. 3, Jan. 1, 2005, pp. 300-308 (9 pages).
R.D. Martins et al, "Effecsts of vitrification of immature bovine oocytes on in vitro maturation", Anim. Reprod., vol. 2, No. 2, Jan. 1, 2005, pp. 128-134 (7 pages).
Corresponding U.S. Appl. No. 61/375,716, filed Aug. 20, 2010.
Du et al, "The cell agglutination agent, phytohemagglutinin-L, improves the efficiency of somatic nuclear transfer cloning in cattle (*Bos taurus*)," Theriogenology, 65, 2006, pp. 642-657, (16 pages).
Gajda et al.,"Oocyte and embryo cryopreservation—state of art and recent developments in domestic animals," Journal of Animal and Feed Sciences, 18, 2009, 371-387. (17 pages).
Song et al., "Vitrification and levitation of a liquid droplet on liquid nitrogen," PNAS Early Edition, 2010, www.pnas.org/cgi/doi/10.1073/pnas.0914059107. (5 pages).
Sung et al.,"Premature Chromosome Condensation Is Not Essential for Nuclear Reprogramming in Bovine Somatic Cell Nuclear Transfer," Biology of Reproduction, 76, 2006, pp. 232-240. (9 pages).
Xu et al.,"Developmental Potential of Vitrified Holstein Cattle Embryos Fertilized In Vitro with Sex-Sorted Sperm," J. Dairy Sci., 89, 2006, pp. 2510-2518. (9 pages).
Australian First Examination Report dated Aug. 2, 2013 issued in corresponding AU Application No. 2011291993 (3 pages).
Australian Examination Report dated Sep. 19, 2013 issued in corresponding AU Application No. 2011291993 (3 pages).

\* cited by examiner

METHOD OF LIQUID NITROGEN SURFACE VITRIFICATION

FIELD

Embodiments of the present invention generally relate to a method for cryopreserving biological material. More particularly, the embodiments relate to a method of producing vitrification droplets for and a method of cryopreserving biological material within vitrification droplets based on fast cooling rates achieved by dropping vitrification droplets in a very cold liquid.

BACKGROUND

Cryopreservation, particularly the cryopreservation of biological samples, refers to the freezing/vitrification of tissues or cells in order to preserve them for future use. Unfortunately, as recognized by those of ordinary skill in the art, cryopreservation and thawing, of biological samples using presently available techniques often is less than optimal, as the biological activity of certain biological samples is often significantly diminished as a result. The practical use of particular biological techniques dictates certain cells are stored for long periods of time. There has been a growing demand for a new method of preserving biological samples, in particular cellular material, such that the biological functionality of the material is preserved after warming. A particular need for the preservation of biological samples has arisen in nuclear transfer and in vitro embryo production.

Cryopreservation provides an instrumental step in the embryo technology field, in particular relating to bovine because embryos can be stored until recipients are synchronized. However, previous cryopreservation techniques either fail to preserve high embryo viability or fail to provide an efficient means for cryopreserving embryos, particularly for bovine embryos produced in vitro.

Conventionally, biological samples were preserved by either slow freezing or by vitrification. The slow freezing technique involves lowering the temperature of a chamber in a stepwise manner. This technique has been used successfully in mouse, human and bovine embryos produced in vivo. However, this process does not work well with in vitro fertilized embryos, and particularly doesn't work well with bovine IVF embryos, possibly due to the different compositions and distributions of proteins and lipids as compared to embryos produced in vivo. Specifically, bovine IVF embryos tend to have high concentrations of lipids because of the cultures in which they are developed. These lipids can result in an embryo which is sensitive to chilling/freezing presumably because the lipids interfere with the intracellular/extracellular exchange of water required for slow freezing. Water and other fluids must be removed during this process or potentially toxic cryopreservatives must be added to prevent intracellular fluids from freezing during the slow freezing process. Otherwise, fluids, such as water, crystallize in a lattice structure which expands from the liquid volume. This expansion causes intracellular stress and mechanical damage to the developing embryonic cellular mass, and can be damaging enough to affect an embryo's viability. The addition of toxic cryoprotectants and attempts to dehydrate IVF embryos mitigate this damage but have yielded less than satisfactory results.

Vitrification provides an alternative means for preservation. Vitrification can be defined as the solidification of a solution brought about not by crystallization, but by extreme elevation in viscosity during cooling. In the case of embryos vitrification has been achieved by freezing the entire embryo so quickly that water molecules do not have time to adjust into a crystallized lattice structure. Instead, the mater molecules remain in their random configuration. By retaining the same ionic and molecular distribution in a glass state chemical and mechanical damage to adjacent intracellular components is avoided.

It is believed that one of the bottlenecks of vitrification technology is the "insufficient" cooling rate of oocytes in current vitrification schemes (Vajta et al., *Embryo Transfer Newsletter* 15: 12-18 (1997)). In order to overcome this problem, several methods have been proposed, which use very small amounts of solution. However, a need still exists for a practical technique for preserving embryos with excellent cooling rates.

So-called "minimum drop vitrification" systems have allowed breakthrough results with bovine and porcine oocyte cryopreservation (See, e.g., Arav A., *Vitrification of oocyte and embryos*, In: Lauria A, Gandolfi F (eds.), *New trends in embryo transfer*, Cambridge, England: Portland Press, 255-264 (1992)). In "minimum drop vitrification" small amounts of solution are placed on a special cryo-stage which is cooled down quickly. This method, unfortunately, has not been found by the art to be convenient for preserving large numbers of oocytes.

Another vitrification technique includes loading a few microliters of vitrification solution into glass capillaries (Dinnyes et al., *Cryobiology* 31: 569-570 (1994)), or into open pulled plastic straws (Vajta et al., *Mol. Reprod. Dev.* 51: 53-58 (1998)) and plunging the capillary or straw quickly into liquid N2. Similarly, vitrification success was achieved by plunging oocyte-containing vitrification solutions with a small loop (Lane et al., *Theriogenology* 51: 167 (1999) (abstr.)). However, such techniques have not been found highly efficient presumably because plunging a warm object into liquid $N_2$ results in the boiling of the liquid and for a short time creates an isolating layer of $N_2$ vapor around the object.

In order to reduce the possibility of an isolating layer of vapor interfering with efficient vitrification, it has been proposed that oocyte-containing vitrification solution be dropped directly into liquid $N_2$. Such technique has been reported to be slightly more effective than prior art vitrification techniques. (Riha et al., *Zivoc. Vir.* 36: 113-120 (1991); Papis et al., *Theriogenology* 51: 173 (1999) (abstr.); Yang et al., *Theriogenology* 51: 178 (1999) (abstr.)), presumably by eliminating the insulation effect of the vapor. However, such technique suffers from the problem of vitrified oocyte retrieval. Specifically, the vitrified oocytes, which can barely be perceivable under normal circumstances, are generally transparent and can be nearly impossible to retrieve in even a few millimeters of liquid. Some groups reported improved success of the cryopreservation of biological materials by using metal surfaces cooled down with the aid of liquid N2. Such metal surfaces are asserted to provide a more efficient heat transfer and to increase further the cooling rates than the cryo-stages used in minimum drop vitrification. Drosophila embryos were successfully preserved by placing them in a metal grid on a cold metal surface (Steponkus et al., *Nature* 345: 170-172 (1990)). Again, presently available techniques employing cooled metal surfaces have not been found convenient for preserving large numbers of oocytes.

U.S. Pat. No. 6,982,172, which is incorporated herein by reference, describes a method for Solid Surface Vitrification (SSV) of oocytes. The patent describes a method including the steps of suspending the oocyte in an equilibrium fluid, rinsing the oocyte in a vitrification medium, and dropping the medium directly on a solid surface cooled to about −150°

Celsius. The step of suspending an oocyte in an equilibrium fluid takes 12-15 minutes as described in this application. Once vitrified, the described technique provides for a single cooling surface, generally limited to about −150° Celsius that creates difficult to manipulate flattened vitrified "pies". Therefore, a need exists for a technique with improved cooling rates not limited by the temperature of a solid surface and a further need exists for an improved cooling rate and an improved system for retrieving vitrified materials.

A further need exists for overcoming the problems of vitrified oocyte retrieval by direct dropping method mentioned above. Still a further need exists for a shortened incubation period and a more efficient method to vitrify a large number of embryos and oocytes. Finally, a need exist to vitrify biological material in a form easier to manipulate compared to flattened pies on a solid surface.

Yet still a further a need exists for a more efficient method to vitrify biological samples, and in particular a faster means to accommodate vitrifying a large number of embryos, which does not suffer drawbacks or difficulty in retrieval.

A need also exists for an improved method of vitrifying sexed embryos, or embryos created with sexed sperm, nuclear transfer embryos, or embryos generated by parthenogenetic activation. Additionally, a need exists for an improved method of vitrifying oocytes, whether oocytes are derived from aspraiation from slaughterhouse ovary, or by ovum pick-up oocyte retrieving from live animals, or derived by stem cells, or induced pluripotent stem (iPS) cells, or by other means.

SUMMARY OF THE INVENTION

Embodiments of the present invention provide a novel method for cryopreserving biological samples, particularly oocytes, embryos, and other cellular materials. The present inventors developed an improved method of producing very small vitrification droplets entraining embryos or oocytes and an improved method for vitrifying and collecting the droplets, or vitrified balls. Combining these elements allows for a droplets vitrified with a very high cooling rate which can be efficiently retrieved. During the warming, the embryos are contacting with warming medium at higher temperature and thereby provides for a very high warming rate.

Embodiments of the present invention further provide an efficient method for vitrifying embryos, or sexed embryos, with superior embryo survivability compared to the conventional slow freezing methods. Post thaw viability of sexed blastocysts have been shown as high as 96% compared to a control of 92%. Excellent hatching rates (84% and 81%) were also determined 72 hours post thaw for both sexed and unsexed blastocysts. After transferring 3,627 of these vitrified-thawed embryos a 41% pregnancy rate was achieved with the vitrified thaws embryos demonstrating vitrification can be used to cryopreserve both sexed and unsexed embryos with minimal damage to the cells.

DETAILED DESCRIPTION THE PREFERRED EMBODIMENTS

Accordingly, a broad object of the invention provides a method for vitrifying cellular material, including embryos and oocytes, with improved cooling rates resulting in improved fertility characteristics. In one embodiment, the method includes a new method for creating a vitrification droplet. The improved vitrification droplet provides a medium which can easily be cooled very quickly, and which can be easily retrieved and manipulated.

Oocytes and embryos can be derived from numerous and varied species of mammal, including without limitation mammals selected from the group of consisting of a human, bovine, equine, porcine, canine, deer, sheep, mouse, rat, rabbit, ferret, buffalo and any species listed by Wilson, D. E. and Reeder, D. M., *Mammal Species of the World*, Smithsonian Institution Press, (1993), hereby incorporated by reference herein.

In one embodiment, the present invention relates to a method of liquid nitrogen surface vitrification of embryos or oocytes which overcomes the short comings of prior art methods. The method can begin by obtaining oocytes through ovum pick up (OPU) techniques, flushing, from slaughterhouse ovaries, stem cell derived oocytes, or iPS cell derived oocytes. Similarly, the method can begin by obtaining embryos by the in vivo or in vitro fertilization of oocytes with sperm. The sperm can be neat sperm, sex sorted sperm, unsorted sperm or a heterogeneous or homogeneous sperm mixture. These embryos can be sexed as male or female by the use of sexed sperm for fertilization. The embryos can be non-sexed, twin embryos, split embryos or chimeric embryos. The embryos can also be produced from nuclear transfer, or cloning. The embryos can be any of: zygotes, cleaved embryos, morulaes, early blastocysts, regular blastocysts, expanding blastocysts, hatching/hatched blastocysts. The blastocysts can be in the 3 to 10 day stages of development, or more preferably in the 5 to 8 day stages of development. The oocytes or embryos can be about between about 100 µm to about 500 µm or higher in diameter.

In one embodiment, following collection, the embryos or oocytes can be treated with solution containing trypsin, as an initial step. Trypsin can be particularly useful in order to remove or deactivate viruses on the zona pellucida. The trypsin solution can be a 0.25% trypsin solution, or another concentration known to be effective in removing or deactivating viruses, for example between about 0.1% trypsin about 0.5% trypsin. It should be further appreciated a similar catalyst for the hydrolysis of peptide bonds can be used. Additionally, the trypsin can serve to thin the zona pellucida, which may improve the cooling rate of embryos consequently improve their ability to be vitrified. Other chemicals known as hyaluronidases can also be used for the same purpose. By way of a non-limiting example, Glycoside hydrolases, such as Disaccharidase and Glucosidases can be used for this purpose. In the alternative, a laser can be used to thin the zona pellucida, or to even puncture the zona pellucida.

It should be appreciated that a trypsin was can be applied to oocytes or embryos as an initial step or between subsequent washing steps, or at the same time as the oocytes or embryos are washed with any of the rinse medium, base medium, hold medium, or vitrification medium.

In one particular aspect, the embryos or oocytes can then be washed with 3-4 mL of a rinse medium comprising 5%-20% FBS M199 solution. However, mediums containing 5%-20% FCS M199, 5%-20% BSA M199, 5%-20% FBS TL Hepes, 5%-20% FBS DPBS, and other similar mediums known to those of skill in the art can also be used. Additionally, various volumes, such as about 1 mL to about 20 mL, can be used. The embryos or oocytes can be washed between 1 and 12 times with this solution, and in one embodiment they can be washed 3 times.

By way of a non-limiting example, the embryos or oocytes can then be washed in 3-4 mL of a solution comprising a rinse medium. The rinse medium can include TCM199 or DPBS supplemented with fetal bovine serum, or bovine serum albumin, or PVA. The embryos or oocytes can be washed for about one minute to about fifteen minutes and can be carried out at temperatures between about 20° C. and about 45° C.

Next the oocytes or embryos can be incubated in 3-4 mL of a base medium for between 1 and 3 minutes. The incubation can be carried out between about 20° C. and about 45° C. The base medium can contain an amount of FBS, as well as glucose, sodium pyruvate and calcium ions.

The oocytes or embryos can then be incubated in hold medium. This step can occur at temperatures between about 25° C. and 45° C., and more preferably between about 37° C. and 40° C. It should be appreciated these values can change slightly from species to species and an exemplary target temperature can be within a few degrees of any natural in vivo embryo temperatures for any particular species. Incubation in the hold medium can last from about 30 seconds to about 10 minutes, and more preferably between about 1 minute and about 5 minutes.

The at least one embryo, or oocyte, can then be washed in a about a 10-20 µl vitrification medium for between about 5 seconds and about and 10 minutes, and more preferably between about 15 seconds and about 60 seconds. This step can also occur in a temperature range near an in vivo embryos temperature, for example between about 25° C. and 45° C., and more commonly between about 37° C. and 40° C. In the case of bovine, this should at or within a few degrees of 39° C.

Once rinsed, the embryos or oocytes can be formed into a droplet with the use of a pipette. The droplet can be formed by aspirating vitrification medium into a channel of a pipette, or another instrument with a channel, such as a glass or plastic tip, followed by aspirating air into the channel, and finally followed by aspirating vitrification medium containing embryos or oocytes into the channel. Expelling the vitrification medium, the air, and the vitrification medium containing embryos from the channel forms a vitrification droplet at the tip of the pipette which can contain an air bubble. The air-bubble contained within the vitrification droplet helps prevent embryos from sticking on the wall of channel. The volume of the vitrification medium aspirated should provide for a vitrification droplet having a volume between 0.2 µL to about 12 µL, and more preferably a volume between about 1 µL and about 2 µL.

The vitrification droplet is then dropped into liquid nitrogen, which can be contained in a tea-tin like container, where vitrification occurs at a very rapid rate forming a vitrification ball. The vitrification ball retains the air bubble which can reflect light so that the vitrification ball can be easily identified in the liquid nitrogen. The vitrification droplet can travel between about 1 cm and about 60 cm from the pipette or other instrument to the liquid nitrogen, and more preferably from about 10 to about 20 cm. Additionally, the vitrification medium can contain a red color indicator, such as, phenol red at the concentration of 5-20 µg/mL, at preferable of 8-10 µg/mL. In this way, the vitrified ball can show a pink-red color in the liquid nitrogen.

The tea-tin like container can have an edge height of about 0.2-10 cm, and preferably about 0.5-1.0 cm for loading a thin layer of liquid nitrogen. The thickness of liquid nitrogen can be about 0.1-5 cm, and preferably about 0.2-0.5 cm. It should be appreciated other containers are contemplated for use herein and the container need only be cable of holding a thin layer of liquid nitrogen. In one embodiment the container can have a first storage part for receiving vitrified balls in a thin layer of liquid nitrogen, and a second storage part containing more liquid nitrogen or other coolant for keeping the liquid nitrogen sufficiently cool in the first storage part.

The vitrification ball can float on the surface of liquid nitrogen due to the air bubble, but can be immersed into liquid nitrogen by tipping the vitrification ball with fine tip forceps. The vitrification ball is generally round in shape based on the method from which it was produced. This round sized vitrification ball is easily picked up by fine tip forceps, thus in combination with the air bubble or dye provides an improvement in handling embryos by dropping method mentioned above.

It should be appreciated that each of the container configuration, the inclusion of dye, and the introduction of an air bubble into the vitrification droplet provide improvements which can be used individually or in combination in order to overcome the prior art difficulties in retrieving vitrified materials.

The formed vitrification droplet with embryos or oocytes can have from 1 to about 50 embryos or oocytes, and more preferably from about 1 to 5 embryos or oocytes.

The vitrified ball can be formed by dropping the vitrification droplet into a thin layer of liquid nitrogen (0.1-5 cm, preferable as 0.2-0.5 cm) which can cover the top of a liquid nitrogen cooled metal cube, plastic cube, or any kind cube that contains liquid nitrogen. The layer of liquid nitrogen should be deep enough to fully submerge the droplet, but should be shallow enough so that vitrified drops can easily be removed with forceps, pipettes or other instruments.

The vitrified droplets can be collected from the liquid nitrogen with liquid nitrogen cooled forceps, pipettes or other tools for placement into cryovials or straws for storage. While moving the vitrified drop, the drop can be maintained between about 0.5 cm about 20 cm above the surface of the liquid nitrogen in order to prevent subsequent inadvertent thawing. Likewise subsequent storage cryovials can be between about 0.5 cm and about 50 cm from the vitrified balls, and more preferably about 1 cm to about 5 cm. Once the vitrified balls are in their subsequent storage container the container can be stored in liquid nitrogen or in liquid nitrogen vapor in order to preserve the vitrified condition.

In one embodiment the volume of the vitrification droplet with at least one embryo or at least one oocyte is coordinated with the density of the vitrification medium in order to ensure vitrification occurs at a sufficient rate when the droplet contacts the water to prevent intracellular ice formation. Once dropped into the liquid nitrogen, the temperature change can occur in the droplet at rate greater than $1\times10^3$ C/min, $1\times10^5$ C/min, or even $1\times10^7$ C/min to ensure vitrification occurs without the formation or ice crystals.

The vitrification droplet can also be formed with a specified volume relative to the volume of embryos entrained therein. For example the ratio of the embryo volume to the total volume of medium containing embryo can be less than 0.75, less than 0.5, less than 0.25, less than 0.1, less than 0.05 or even less than 0.01.

Each of the rinse, base and hold mediums can include dimethyl sulfoxide, ethylene glycol and fetal bovine serum (FBS). The concentration of dimethyl sulfoxide or ethylene glycol can be serially increased in each of the rinse medium and the base medium during the vitrification process.

The vitrification medium can comprise between about 10% and 25% dimethyl sulfoxide, between about 10% and about 25% ethylene glycol, between about 10% and 25% fetal bovine serum (FBS), between about 0.5 g/L and 5 g/L D-glucose, between about 15 mg/L and 100 mg/L sodium pyruvate, between about 5 μg/mL and 20 μg/mL phenol red, between about 0.2 M and 1 M trehalose, and between about 0.2 M and 1.0 M sucrose in DPBS or TCM 199.

Another embodiment of the present invention relates to a method of vitrification which can include the vitrification medium (VM) published in public domains or commercially available for use. Examples of such mediums are: (1). VM1: 2.5 M glycerol, 5.5 M ethylene glycol; (2). VM2: 3.0 M methanol, 6.0 M ethylene glycol; (3). VM3: 1.5 M propylene glycol, 6.0 M ethylene glycol; (4). VM4: 2.0 M propylene glycol, 5.5 M ethylene glycol; (5). VM5: 3.5 M propylene glycol, 4.5 M ethylene glycol; (6). VM6: 3.0 M glycerol, 3.0 M propylene glycol; (7). VM7: 3.0 M ethylene glycol, 4.0 M dimethylsulfoxide; (8). VM8: 1.0 M butylenes glycol, 6.0 M ethylene glycol; (9). VM9: 1.8 M glycerol, 6.1 M ethylene glycol; (10). VM10:1.5 M glycerol, 6.5 M ethylene glycol; (11). VM11: 1.8 M glycerol, 6.0 M ethylene glycol; (12). VM 12: 1.5 M glycerol, 6.3 M ethylene glycol; (13). VM 13: 5.6 M ethylene glycol; (14). VM 14: 8.0 M ethylene glycol; (14). VM 14: 3.2 M ethylene glycol, 2.6 M dimethylsulfoxide. Each of these vitrification media can be used for liquid nitrogen surface vitrification.

Another embodiment of the present invention relates to a method of warming vitrified materials, such as materials vitrified within vitrified balls, which can include vitrified embryos or vitrified oocytes. The process can begin by obtaining vitrified balls containing embryos or oocytes. The vitrified balls containing vitrified oocytes or embryos can be formed in a process as previously described and sorted in straws or cryovials which are cooled with liquid nitrogen or liquid nitrogen vapor.

The vitrified balls can be placed in a warming medium, with nitrogen cooled prongs and oocytes or embryos can be collected from the medium within about 5 seconds to about 5 minutes and more preferably within about 30 seconds to about 1 minute. The vitrified ball can be dropped into the warming medium from about 1 cm to about 60 cm, and more preferably from between about 5 cm and about 10 cm. The warming medium can be between about 25° C. and about 42° C., and more preferably between about 37° C. and about 40° C. In particular, the temperature can be within a few degrees of in vivo embryo temperatures for any particular species.

Upon collection the oocytes or embryos can be moved into a rehydration medium for about 1 minute to about 10 minutes and more preferably for about 3 minutes to about 4 minutes. The rehydration medium can be kept between about 25° C. and about 42° C., and more preferably between about 37° C. and about 40° C.

The rehydrated embryos can be moved into a base medium for about 1 minute to about 10 minutes and more preferably for about 3 minutes to about 4 minutes. The base medium can be kept between about 25° C. and about 42° C., and more preferably between about 37° C. and about 40° C.

The rehydrated embryos can then be moved into a rinse medium for about 1 minute to about 10 minutes and more preferably for about 3 minutes to about 4 minutes. The rinse medium can be kept between about 25° C. and about 42° C., and more preferably between about 37° C. and about 40° C.

EXAMPLE 1

LNSV for Unsorted Embryos

Cryopreservation of Pre-Selected Female Embryos

Embryos were cryopreserved by LNSV. Briefly, bovine blastocysts were serially incubated in Rinse, Base, and Hold medium for 3 min prior to vitrification of 4 to 5 embryos in a 2-μL Vitrification medium droplet, by direct placement onto a thin layer of liquid nitrogen on the solid surface of a metal plate. A group of 30 to 50 vitrified embryos were then transferred into a small freezing vial with a cold fine tipped forceps, sealed, and stored in the vapor phase of liquid nitrogen (−150° C.).

In Vitro Evaluation of Vitrified Female Holstein Embryos

In order to test the viability of vitrified embryos, frozen embryos were sequentially warmed, rehydrated, and washed in Warm, Rehydrate and Base media at 39° C. for 5 minutes each. Embryo survival was evaluated morphologically under stereomicroscopy when embryos were still at a live state and without any fixing treatment. Frozen-thawed embryos were cultured in vitro for 3 days under cumulus co-culture containing 10% FBS (Fetal Bovine Serum) M199 culture medium, and the survival or hatching rates were recorded at 0, 24, 48, and 72 hours. At 72 hour of culture, 25 hatched blastocysts from each treatment were stained by Hoechst and analyzed under fluorescence microscopy for cell counts.

EXAMPLE 2

Embryo Transfer of Female Blastocysts (Sex Sorted)

Vitrified presumptive female bovine IVF embryos were transferred into recipients to examine their developmental potential in vivo. Recipient cattle breeds consisted of Chinese Native Yellow Cattle and Holstein cattle in several Chinese farms. Recipients were chosen according to criteria that included: age, health status, breeding history, size and weight, as well as the farm's nutritional management. Recipients were synchronized by a regime of 2 injections of prostaglandin F2α (LUTALYSE®, Upjohn Co., Kalamazoo, Mich.; 25 mg/injection, i.m.) at the interval of 11 days. Corpus luteum (CL) regression and the estrus usually occurred approximately 48 to 72 hours later. The onset of estrus of recipients was monitored closely as standing heat estrus on day 0. On day 7 following estrus, recipients were selected by palpation per rectum to verify the presence and the size of the CL. The vitrified droplets containing the embryos were thawed through a series of steps described above. Blastocysts (one/straw) were loaded into 0.25 mL French straws containing VIGRO™ Holding Plus (AB Technology, Pullman, Wash.). Straws were maintained at 39° C. in a portable incubator for transportation to the farms. A single embryo was deposited non-surgically into the uterine horn ipsilateral to the ovary with the CL. Pregnancy was determined by palpation per rectum on day 70 after transfer. All day 70 pregnancies were carried to term.

TABLE 1

In vitro and in vivo developmental competence of sex-sorted in vitro fertilized (IVF) embryos

| Embryo Type | Embryos (n) | % of post-warming survivability and development of vitrified embryos Mean ± SEM | | | | | Embryo transfer results Mean ± SEM | |
|---|---|---|---|---|---|---|---|---|
| | | 2 h | 24 h | 72 h | Hatched at 72 h | Cell count[1] | No. of Recipients[2] | % Pregnancies[3] |
| Sorted | 164 | 96.4 ± 1.4[a] | 96.3 ± 1.5[a] | 96.3 ± 1.5[a] | 84.4 ± 3.0[a] | 538 ± 35[a] | 3627 | 40.9 ± 3.6[a] |
| Non-sorted | 149 | 93.1 ± 1.5[a] | 91.8 ± 1.5[a] | 91.8 ± 1.9[a] | 80.6 ± 3.7[a] | 515 ± 33[a] | 481 | 41.9 ± 3.0[a] |
| In vivo | N/A | | | | | | 1192 | 53.1 ± 0.5[a] |

[a] Values with same superscript within columns are not different (P > 0.05). Sorted, sexed IVF blastocysts fertilized with sorted X-sperm; Non-sorted, non-sexed IVF blastocysts fertilized with conventional non-sexed semen; In vivo, In vivo embryos cryopreserved by conventional programmed slow freezing protocol; N/A, In vivo derived embryos were not thawed for survivability test.
[1] 25 hatched IVF blastocysts from Sorted and Non-sorted vitrification groups were applied for nuclear evaluation by fluorescent microscopy.
[2] Sexed or non-sexed embryos were vitrified on day 7 after IVF. After thawing, only a single embryo derived from either IVF (sexed or non-sexed) or in vivo flushing was transferred non-surgically into each synchronized recipient.
[3] Pregnancy of recipients was examined by palpation per rectum on day 70 post transfer.

EXAMPLE 3

LNSV-Cloned Embryos, Post Warming Survival

Vitrification of Cloned Embryos

Cloned bovine blastocysts on day 7, usually at the expanding stage comparable to that of normally fertilized embryos, but beginning to hatch through the cuts made on the zona pellucida during NT, were selected for cryopreservation. Embryos were cryopreserved by a modified vitrification protocol, liquid nitrogen surface vitrification (LNSV) described previously. Briefly, bovine NT blastocysts were pre-incubated in serially increased concentrations of dimethyl sulfoxide (DMSO), ethylene glycol (EG) and 20% FBS PBS medium for 3 min, two embryos per group were then vitrified in droplet containing a high concentration of DMSO, EG, and sucrose by directly dropping into a thin layer of liquid nitrogen on the solid surface of a metal plate that generated a super cold surface for vitrification. The vitrified embryo-containing droplets were then transferred into a small freezing vial and stored in the vapor phase of liquid nitrogen (−150° C.). The liquid nitrogen used throughout the LNSV procedure was passed through a ceramic filter to remove microorganisms, the filtered liquid nitrogen was then stored in a tank tested free of viral contamination prior to use.

Figure 1:
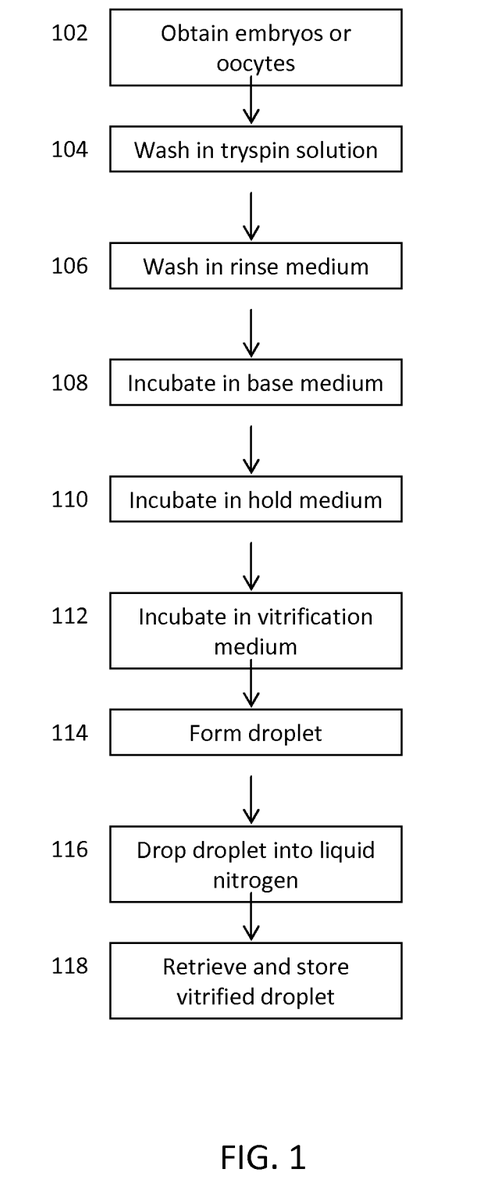
FIG. 1 illustrates a pre-vitrification method in accordance with the present invention.

Referring now to the figures, and particularly to FIG. 1, a diagram illustrates the vitrification steps in accordance with one embodiment of the present invention. At step 102 embryos or oocytes are obtained for vitrification. The oocytes can be collected in any manner described above, or any other manner known to those of ordinary skill in the art. Embryos can also be selected or produced in any manner described above, or produced in any manner known to those in the art. By way of a non-limiting example, the embryos can be sexed embryos in the form of a day 7 extended blastocysts. At step 104 the embryo can then be washed in a trypsin solution. At step 106 the embryos can be washed in a rinse medium for 3 to 12 minutes, and in one aspect between about 3 to about 4 minutes. After washing, the embryos can be incubated in a base medium for 3 minutes at step 108. At step 110, the embryos can be incubated in a hold medium for 1-3 minutes at about 39° C. Next, at step 112, the embryos can be washed in a 10 μL to 20 μL vitrification solution at about 39° C. for about 15 seconds to about 30 seconds. Following this wash, at step 114, a vitrification droplet can be formed with the vitrification medium entraining several embryos. In one embodiment the vitrification droplet formed can be between about 1 μL to 2 μL entraining 1-15 embryos.

Once the vitrification droplet is formed, at step 116 the droplet can be dropped 10-20 cm into liquid phase nitrogen. The liquid nitrogen can be a thin layer of liquid phase nitrogen, with a sufficient depth for submerging the droplet. The density and the volume of the vitrification droplet influence the rate at which liquid nitrogen can cool the droplet and vitrify entrained cells, such as embryos or oocytes. The vitrification medium must be selected in order to ensure the rate of cooling is sufficient for vitrification and that ice crystals are not formed during this process.

At step 118 nitrogen cooled and fine tip forceps can be used to retrieve vitrified balls from the liquid nitrogen. The vitrified balls can also be retrieved with glass pipettes, plastic pipettes and other instruments. Optionally, the instrument can be chilled in order to prevent inadvertent thawing by contact with a relatively warm surface. In order to maintain the vitrified balls in a vitrified state, a subsequent storage container can be located within about 50 cm of the vitrified balls, or even within 5 cm. The retrieved vitrified droplets can then be stored in cryo-vials in liquid or vapor phase nitrogen.

Figure 2:
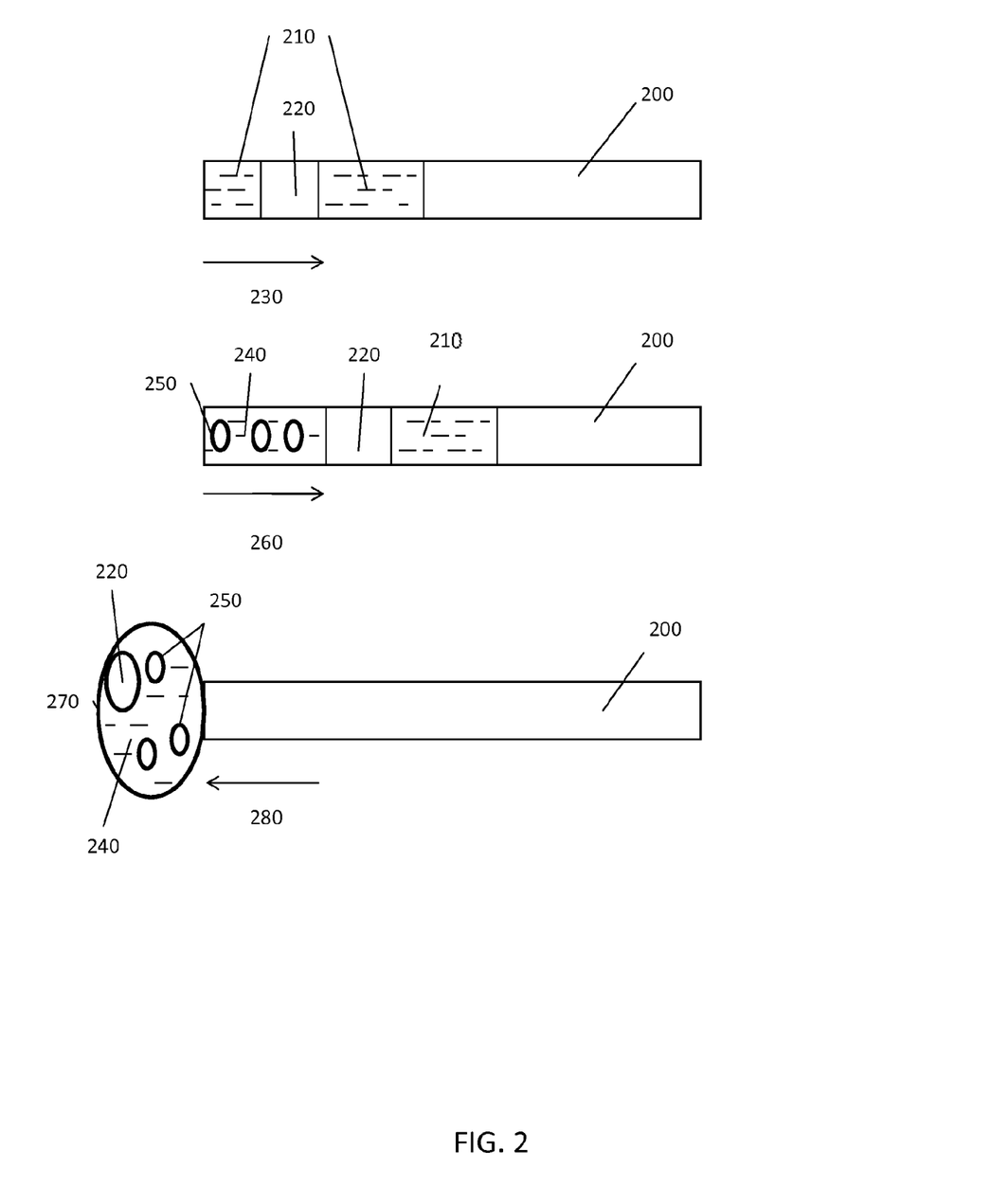
FIG. 2 illustrates the process for producing vitrified balls in accordance with certain embodiments of the present invention.

Turning now to FIG. 2 a more detailed illustration of the method of droplet formation is provided. An instrument 200, which can be a glass pipette, a plastic pipette, or another instrument with a channel aspirates two portions of vitrification medium 210, separated by air 220. The direction of the aspiration is indicated by arrow 230. The vitrification medium can be any of those previously described.

Embryos, oocytes or other biological samples 250 are aspirated into the instrument 200 as indicated by arrow 260 forming an entrained vitrification medium 240 separated from vitrification medium 210 by air 220. The embryos, oocytes, or other biological samples can be produced or collected in any of the manners previously disclosed, or by any other means known to those in the art. It should be understood another intermediary fluid can be used in place of air, and the term intermediary fluid is intended to cover both a gas and liquid interjected between the two parts of vitrification fluid. By way of a non-limiting example, a gas such as nitrogen or oxygen case also be used, but fluids also contemplated.

The vitrification droplet 270 is formed by expelling the entrained vitrification medium 240, air 220 and vitrification medium 210 from the instrument as indicated at arrow 280. The formed vitrification droplet 270 retains an air bubble 220, and an entrained biological sample 250. As described previously, the vitrification droplet can range in volume from between about 0.2 µL to about 12 µL, and can entrain from about 1 to about 50 oocytes or embryos.

The air bubble helps ensure successful droplet formation. The air bubble further provides a contrast to the transparent vitrified ball and is reflects light differently, thereby providing a visual indication of the vitrified ball. This visual indication is particularly useful when the vitrified ball is displaced in a fluid, such as liquid nitrogen. The air bubble further provides a slight upwards buoyancy force making the vitrified ball both easier to see and easier to handle.

As previously described, the vitrification medium can further contain a dye in order to further assist in locating vitrified droplets in liquid nitrogen.

Figure 3:
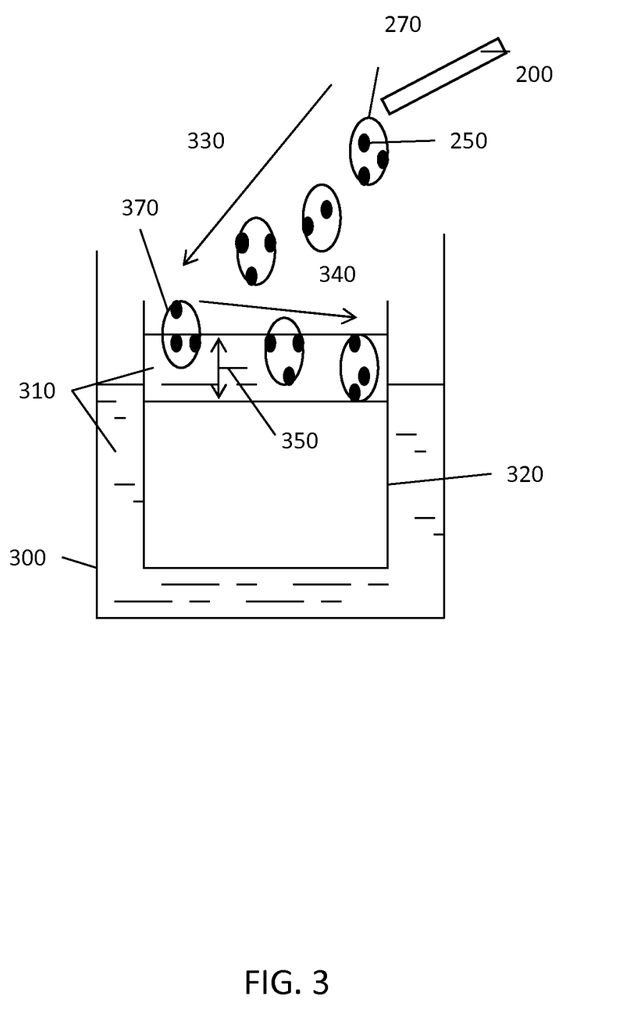
FIG. 3 illustrates a method and apparatus for producing vitrified droplets in accordance with certain embodiments of the present invention.

Turning now to FIG. 3 a metal block, or tea tin or cover or any kind of cylinder 320 can be placed in a container 300 with liquid nitrogen 310 providing a shallow layer of liquid nitrogen 350. The instrument 200 can form a vitrification droplet 270 directly above the shallow layer of liquid nitrogen 350 for dropping the vitrification droplet about 10 cm into the liquid nitrogen as illustrated along arrow 330. Once in the thin layer of liquid nitrogen 310 the vitrification droplet 270 forms a vitrified ball 370 entraining biological sample and can sink to the top surface of the metal block or, or tea tin or cover or any kind of cylinder 320, along arrow 340. Because of the slight increase in buoyancy an air bubble can provide, the vitrified ball 370 may actually be pushed with forceps or a pipette in order to ensure the vitrified ball 370 is submerged in liquid nitrogen. This arrangement provides a sufficiently thin nitrogen layer, so that vitrified drops can be manipulated and recovered while preventing the thin layer of liquid nitrogen from evaporating too quickly.

Figure 4:
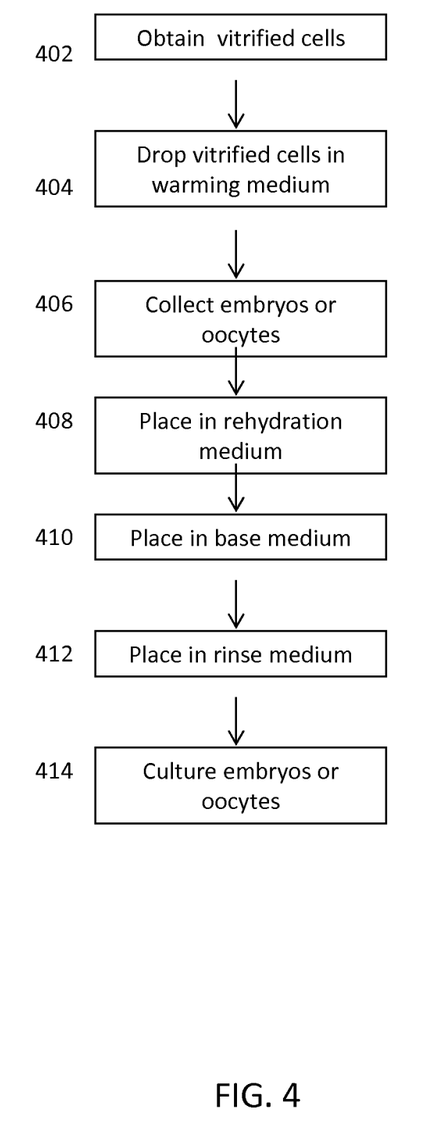
FIG. 4 illustrates a method for warming vitrified embryos in accordance with certain embodiments of the present invention.

FIG. 4 illustrates an outline for a method of warming vitrified embryos or oocytes. At step 402 vitrified embryos or oocytes are obtained. The embryos or oocytes can be obtained from straws or cryovials stored in liquid nitrogen or in liquid nitrogen vapor. The vitrified embryos or oocytes can be entrained within vitrified droplets or vitrified balls stored in liquid nitrogen vapor.

At step 404, the vitrified embryos can be directly dropped into a warming solution. The warming medium can be kept at about 39° C. for the purpose of thawing bovine embryos or oocytes. It can be appreciated by those in the art to use different temperatures for different species. The warming medium can be kept at a relatively constant temperature with a hot plate.

At step 406, the embryos or oocytes are collected from the warming medium with a pipette. The embryos or oocytes can be collected within about 15 seconds to about 5 minutes of being dropped in the warming medium, and more preferably with about 15 seconds to about 1 minute of being dropped.

At step 408, the embryos or oocytes are placed into a rehydration solution with a pipette and incubated for about 1 minute to about 10 minutes at about 39° C., and more preferably for about 3 minutes to about 4 minutes.

At step 410, the embryos or oocytes are placed into a base solution with a pipette and incubated for about 1 minute to about 10 minutes at about 39° C., and more preferably for about 3 minutes to about 4 minutes.

At step 412, the embryos or oocytes are placed into a rinse solution with a pipette and incubated for about 1 minute to about 10 minutes at about 39° C., and more preferably for about 3 minutes to about 4 minutes.

At step 414, the embryos or oocytes are placed into culture medium with a pipette and incubated about 39° C., under the humid 5% $CO_2$ in air, and/or the embryos are loaded for embryo transfer or any biological works. Oocytes are used for IVF, activation, nuclear transfer or any biological works.

As can be easily understood from the foregoing, the basic concepts of the present invention may be embodied in a variety of ways. The invention involves numerous and varied embodiments of shipping container and methods of making and using the shipping container including, but not limited to, the best mode of the invention.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

Moreover, for the purposes of the present invention, the term "a" or "an" entity refers to one or more of that entity; for example, "an embryo" refers to one or more of the embryos. As such, the terms "a" or "an", "one or more" and "at least one" can be used interchangeably herein.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

The invention claimed is:

1. A method of forming a vitrification droplet comprising the step of:
   a) aspirating vitrification medium into a channel;
   b) aspirating an intermediary fluid into the channel, wherein the intermediary fluid comprises air or a gas;
   c) aspirating vitrification medium containing at least one embryo or at least one oocyte into the channel; and
   d) expelling the vitrification medium, the air, and the vitrification medium containing the at least one embryo or at least one oocyte from the channel to form a vitrification droplet at the end of the channel, wherein the vitrification droplet contains at least one air bubble and at least one embryo or oocyte.

2. The method according to claim 1, wherein the vitrification medium and the vitrification medium containing at least one embryo are separated by the intermediary fluid in the channel prior to the step of expelling.

3. The method according to claim 1, wherein the step of expelling vitrification medium, the intermediary fluid, and the vitrification medium containing the at least one embryo or at least one oocyte from the channel results in a vitrification droplet formed at the end of the channel entraining the at least one embryo or at least one oocyte.

4. The method of claim 1, further comprising the step of dropping the vitrification droplet into liquid nitrogen.

5. The method according to claim 4, wherein the vitrification droplet is dropped from between about 5 cm and about 60 cm into the liquid nitrogen.

6. The method of claim 4, wherein the vitrification droplet is dropped into the liquid nitrogen from a distance between about 0.1 cm and 5 cm.

7. The method according to claim 1, further comprising the step of incubating the vitrification medium at between about 37° C. and 42° C. prior to the steps of aspirating.

8. The method according to claim 1, wherein the vitrification medium includes a coloring dye.

9. The method according to claim 1, wherein the at least one embryo or at least one oocyte comprises an embryo which has been produced from sex selected sperm.

* * * * *